(12) United States Patent
Elmaleh

(10) Patent No.: US 8,801,777 B2
(45) Date of Patent: Aug. 12, 2014

(54) INTRAVASCULAR DEVICE WITH NETTING SYSTEM

(76) Inventor: David Elmaleh, Newton, MA (US)

( * ) Notice: Subject to any disclaimer, the term of this patent is extended or adjusted under 35 U.S.C. 154(b) by 288 days.

(21) Appl. No.: 11/788,008

(22) Filed: Apr. 18, 2007

(65) Prior Publication Data

US 2008/0262598 A1 Oct. 23, 2008

(51) Int. Cl.
*A61F 2/06* (2013.01)

(52) U.S. Cl.
USPC ........ 623/1.39; 623/1.13; 623/1.44; 623/1.16

(58) Field of Classification Search
USPC ............................................... 623/1.13, 1.39
See application file for complete search history.

(56) References Cited

U.S. PATENT DOCUMENTS

| | | | | |
|---|---|---|---|---|
| 5,639,278 | A * | 6/1997 | Dereume et al. | 623/1.13 |
| 6,240,616 | B1 * | 6/2001 | Yan | 29/527.2 |
| 6,245,100 | B1 * | 6/2001 | Davila et al. | 623/1.13 |
| 6,296,661 | B1 * | 10/2001 | Davila et al. | 623/1.13 |
| 6,315,794 | B1 * | 11/2001 | Richter | 623/1.34 |
| 6,551,350 | B1 * | 4/2003 | Thornton et al. | 623/1.13 |
| 6,632,240 | B2 | 10/2003 | Khosravi et al. | 623/1.13 |
| 2002/0045931 | A1 * | 4/2002 | Sogard et al. | 623/1.13 |
| 2003/0149475 | A1 | 8/2003 | Hyodoh et al. | |
| 2003/0195556 | A1 | 10/2003 | Stack et al. | |
| 2005/0137677 | A1 | 6/2005 | Rush | 623/1.13 |
| 2006/0036308 | A1 | 2/2006 | Goshgarian | 623/1.11 |
| 2006/0184237 | A1 * | 8/2006 | Weber et al. | 623/1.44 |
| 2006/0248871 | A1 | 11/2006 | Johnson et al. | 57/58.83 |
| 2006/0271169 | A1 | 11/2006 | Lye et al. | 623/1.19 |

OTHER PUBLICATIONS

PCT International Search Report based on PCT/US2008/005001 dated Oct. 9, 2008.

* cited by examiner

*Primary Examiner* — David Isabella
*Assistant Examiner* — Jacqueline Woznicki
(74) *Attorney, Agent, or Firm* — Thomas J. Osborne, Jr., PC; Thomas J. Osborne, Jr.

(57) ABSTRACT

An intravascular device for keeping open a previously constricted site within a vessel and for minimizing tissue debris at such a site from closing off the vessel is provided. The device includes an expandable substantially tubular body having a distal end and a proximal end. The device also includes a flexible netting system that is circumferentially disposed about the body, and extends beyond at least one of the distal end or proximal end. The netting system can expand along with the body to minimize release of tissues debris at the site from closing the lumen of the vessel. The netting system can include a plurality of pores to permit communication between fluid flow within the vessel and the vessel wall, and at least one pharmacotherapeutic agent for the treatment or prevention of certain conditions. A method for placing the device at a site of interest is also provided.

12 Claims, 9 Drawing Sheets

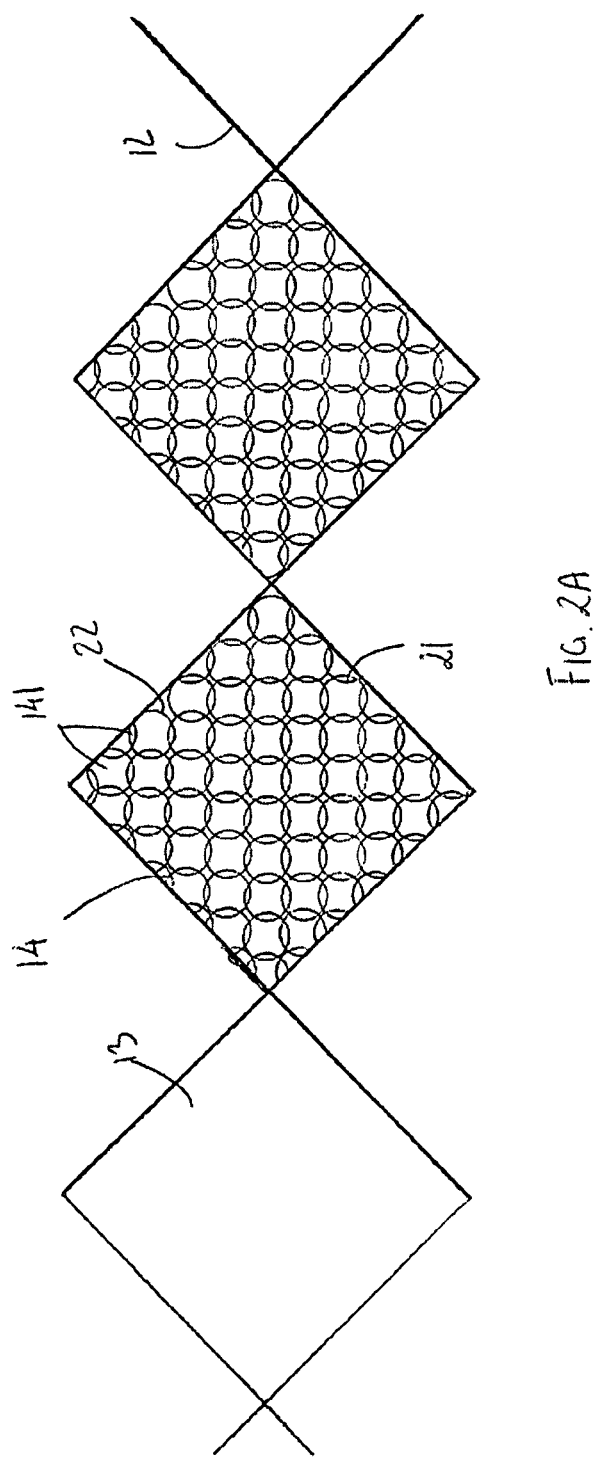

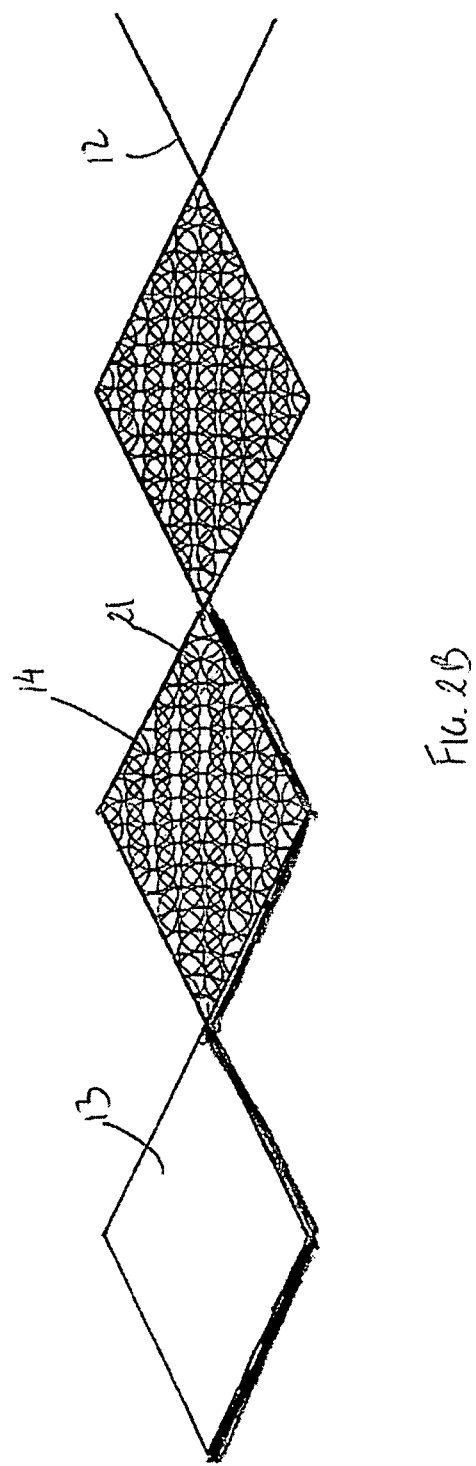

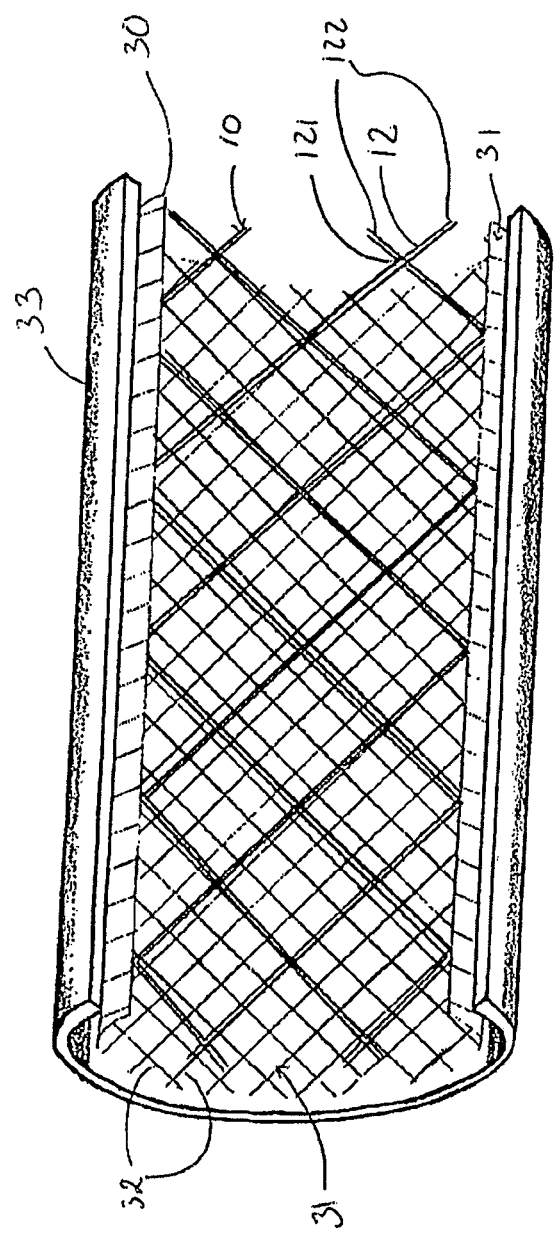

INTRAVASCULAR DEVICE WITH NETTING SYSTEM

FIELD OF THE INVENTION

The present invention relates to intravascular devices, and more particularly, to stents for maintaining an open lumen within a vessel and for minimizing thrombus formation as well as release of tissue debris therefrom to prevent blockage of fluid flow within the vessel.

RELATED ART

Many medical intravascular devices are currently being used either temporarily or permanently inside the human body to address conditions associated with high blood pressure, diabetes, and stroke. One example of an intravascular device is a stent for use in, for instance, coronary angioplasty. Stents are small mechanical devices that can be implanted within a vascular structure, such as a blood vessel or an artery, and can be mechanically expanded to maintain an open lumen at a constricted location to permit a substantially clear flow path therethrough. A stent can also act to support a vessel wall in areas vulnerable to collapse.

The mechanical reopening of a constricted vessel can sometimes lead to injuries of the tissues at the site of constriction or closure. Such injuries can often stimulate thrombus formation at such a site, as well as release of tissue debris that may subsequently act to block fluid flow within the vessel. Moreover, if permitted to proliferate, pronounced neointimal hyperplasia or restenosis can result. Thrombus production remains one of the most common post-stenting clinical problem, and requires effective intervention or counter-measures to prevent and/or control its reoccurrence.

Currently, methods for preventing or controlling thrombus are specifically aimed at influencing factors believed to be involved in the body's response to external or internal tissue stimulants, such as angioplasty, stenting procedures, and/or viruses. Common countermeasures which have been used to prevent or control restenosis generally fall into the one of several categories, including (1) mechanical atheroablative techniques, such as debulking, vascular filters, and embolitrapping devices, (2) ultrasound-initiated atheroablative techniques, (3) light-assisted procedures, predominantly excimer laser angioplasty, (4) pharmacological agents and gene therapy, (5) ultraviolet photophoresis, believed to be an immune modulator, (6) radiation therapy, such as external and endovascular brachytherapy, and (7) re-stenting.

In addition, modifications to stent designs and materials have been proposed to prevent and/or control restenosis. In one approach, non-metallic, biodegradable stent materials, such as high molecular weight Poly-l-lactic acid (PLLA) is used.

Numerous inorganic coatings and surface treatments have also been developed to improve chemical inertness and biocompatibility of metallic stents. Some coatings, such as gold, however, yield a higher rate of in-stent restenosis than uncoated stents. Others, including silicon carbide and turbostatic carbon, show promise but additional studies must be done.

Organic coatings, including both synthetic and natural coatings, have also been widely studied. Among the synthetic coatings studied are Dacron, polyester, polyurethane, polytetrafluoroethylene (PTFE), polyethylacrylate/polymethylmethacrylate, polyvinyl chloride, silicone, collagen, and iridium oxide. Results of studies, such as those with PTFE-coated stents, are disappointing or mixed at best, as there are high occurrences of late thrombo-occlusive events. With only a very few exceptions, the general consensus is that any favorable outcome was not associated with treatment of conventional in-stent restenosis using PTFE-coated stents.

Intracoronary intervention have also been employed to reduce neointima formation by reducing smooth muscle cell proliferation after balloon angioplasty. However, such intervention is often complicated by subacute and late thrombosis. Coronary thrombo-aspdrugiration and coronary pulsed-spray procedures, followed by immediate endovascular therapy, have also been particularly helpful in removing thrombotic material associated with plaque.

In addition, pharmacotherapeutic agents have been used for the treatment of some of the major post-angioplasty complications, including immunosuppressants, anticoagulants and anti-inflammatory compounds, chemotherapy agents, antibiotics, antiallergenic drugs, cell cycle inhibitors, gene therapy compounds, and ceramide therapy compounds. Pharmacotherapeutic agents can be delivered either systemically or locally. Systemic treatment has shown limited success in reducing restenosis following stent implantation, a result believed to be due to inadequate concentration of the pharmacotherapeutic agents at the site of injury. Increased dose administration, however, is constrained by possible systemic toxicity. It has been observed that local delivery of higher doses via drug eluting stents can significantly reduce adverse systemic effects. However, the local delivery of drugs via stents may be limited by the amount of surface area for drug elution.

Gene therapy have also been employed in the treatment of thrombus production. The procedure is directed towards smooth muscle cells and involves gene transfer via DNA, with or without integration of chromosomes, into selected cells. In transduction without integration, the gene is delivered to both cytoplasm and nucleus and is therefore non-selective. Gene transfer for integration employs retrovirus to affect growth stimulators.

Antibiotics, likewise, has been used in the treatment of coronary artery disease. It is known that antibiotics are effective in controlling inflammation caused by a variety of infectious agents found in fatty plaques blocking the arteries. Results of clinical investigation, such as with azithromycin, suggest a modest antibiotic benefits for heart patients.

Similarly, a phospholipid exhibiting immunosuppressive properties, has been shown to block T-cell activation and proliferation, inhibit Taxol-induced cell cycle apoptosis, and activate protein kinase signal translation in malignant myogenic cells. Rapamycin and its analogs exhibit anti-tumor activities at relatively low dose levels, while inducing only mild side effects, an extremely important aspect of patient care.

SUMMARY OF THE INVENTION

The present invention provides, in one embodiment, an intravascular device, such as a stent, for keeping open a previously constricted intravascular site within a vessel and for minimizing tissue debris from such a site from closing off the vessel. The device may also be used for local delivery of at least one pharmacotherapeutic agent to the intravascular site for the treatment or prevention of restenosis.

The intravascular device, in accordance with an embodiment of the invention, includes an expandable substantially tubular body for placement against a vessel wall. The body of the device, in an embodiment, can be defined by a framework having a plurality of openings. The device also includes a flexible netting system having a structural design for extending across each of the openings. Such a design allows the netting system to expand along with each opening in the framework to minimize occurrence of thrombus formation and tissues debris from closing the lumen of the vessel. The netting system can include a plurality of pores to permit communication between fluid flow within the vessel and the vessel wall, and at least one pharmacotherapeutic agent for the treatment or prevention of certain conditions. In one embodiment, the netting system includes a plurality of extensible panels, each designed to be securely situated within an opening of the matrix. Alternatively, the netting system includes a mesh disposed on a substantially flexible matrix, such that the mesh can be placed circumferentially about the framework of the body. If desired, the flexible matrix can be provided with sufficient strength to permit the netting system to keep the lumen of the vessel temporarily open until the framework can be expanded. The device of the present invention, in an embodiment, can further include a second expandable substantially tubular framework concentrically positioned within the first framework of the tubular body.

The present invention also provides a method for the placement of an intravascular device within a vessel. The method includes initially providing a device having an expandable substantially tubular body defined by a framework having a plurality of openings, and a plurality of netting panels situated within each of the openings. Next, the device may be advanced along a lumen of the vessel to a site of interest. Thereafter, the framework may be expanded at the site of interest to allow the lumen of the vessel to remain open. The device may subsequently act to elute at least one pharmacotherapeutic agent for treatment of a condition from the netting panels. The netting panels may also act to retain tissue debris between the netting panels and a vessel wall.

The present invention further provides another method for placement of an intravascular device within a vessel. The method includes providing a device having an expandable substantially tubular body defined by a framework having a plurality of openings, and a mesh disposed on a substantially flexible matrix loosely positioned circumferentially about the framework. Next the device may be advanced along a lumen of the vessel to a site of interest. Thereafter, the framework may be expanded at the site of interest, and the mesh on the flexible matrix be allowed to be secured between the framework and a vessel wall. In one embodiment, prior to expanding the framework, the flexible matrix on which the mesh is disposed may be expanded. The device may subsequently act to elute, from the mesh, at least one pharmacotherapeutic agent for treatment of a condition. The mesh may also act to retain tissue debris between the netting panels and a vessel wall.

In another embodiment, a further method for placement of an intravascular device within a vessel is provided. The method includes initially providing a device having a first expandable, substantially tubular framework having a plurality of openings, a plurality of netting panels situated within each of the openings, and a second expandable substantially tubular framework concentrically positioned within the first tubular framework. Next, the device may be advanced along a lumen of the vessel to a site of interest. Thereafter, the device may be expanded at the site of interest to allow the lumen of the vessel to remain open. In one embodiment, the first and second tubular framework may be expanded independently. Alternatively, the first and second tubular framework may be expanded simultaneously. The device may subsequently act to elute at least one pharmacotherapeutic agent for treatment of a condition from the netting panels. The netting panels may also act to retain tissue debris between the netting panels and a vessel wall.

In another embodiment, the present invention provides an intravascular device for maintaining an open lumen within a vessel. The device can include an expandable substantially tubular body for placement against a vessel wall. The body can have a distal end and a proximal end. The device can also include a flexible netting system, which can be circumferentially disposed about the tubular body to reduce the occurrence of thrombus formation, and tissue debris from closing the lumen of the vessel. The netting system can extend beyond at least one of the distal end or proximal end. The extended portion of the netting system can provide cushioning between the distal end or proximal end of the body and the vessel wall, to reduce risk of abrasion to the vessel wall by the distal end or proximal end being pushed into the vessel wall when the device is advanced and expanded in the vessel. The netting system can also have a smooth surface to minimize protrusion of tissue into the lumen, in order to reduce turbulence of fluid flow within the lumen of the vessel.

In another embodiment, another method for placement of an intravascular device within a vessel is provided. The method includes providing a device having an expandable substantially tubular body having a distal end and a proximal end, and a flexible netting system circumferentially disposed about the tubular body, and extending beyond at least one of the distal end or proximal end, to reduce occurrence of thrombus formation and tissue debris from closing a lumen of the vessel. Next, the device can be advanced along the lumen of the vessel to a site of interest. Thereafter, the device can be expanded at the site of interest to allow the lumen of the vessel to remain open.

In another embodiment, the present invention provides an intravascular device for maintaining an open lumen within a vessel. The device can include an inner stent having an expandable substantially tubular body for placement against a vessel wall. The body having a distal end and a proximal end. The device can also include an outer stent having a smooth porous surface, which can be circumferentially disposed about the tubular body to minimize protrusion of tissue into the lumen to reduce turbulence of fluid flow within the lumen of the vessel. The outer stent can extend beyond at least one of the distal end or proximal end. The extended portion of the outer stent can act as a barrier between the distal end or proximal end of the body and the vessel wall, to reduce risk of abrasion to the vessel wall by the distal end or proximal end being pushed into the vessel wall when the device is advanced and expanded in the vessel.

BRIEF DESCRIPTION OF THE DRAWINGS

FIGS. 2A-B illustrate a detailed view of a portion of the device in FIG. 1 with a netting system in accordance with an embodiment of the present invention.

FIG. 3 illustrates a longitudinal section view of another intravascular device in accordance with one embodiment of the present invention.

DETAILED DESCRIPTION OF SPECIFIC EMBODIMENTS

Figure 1:
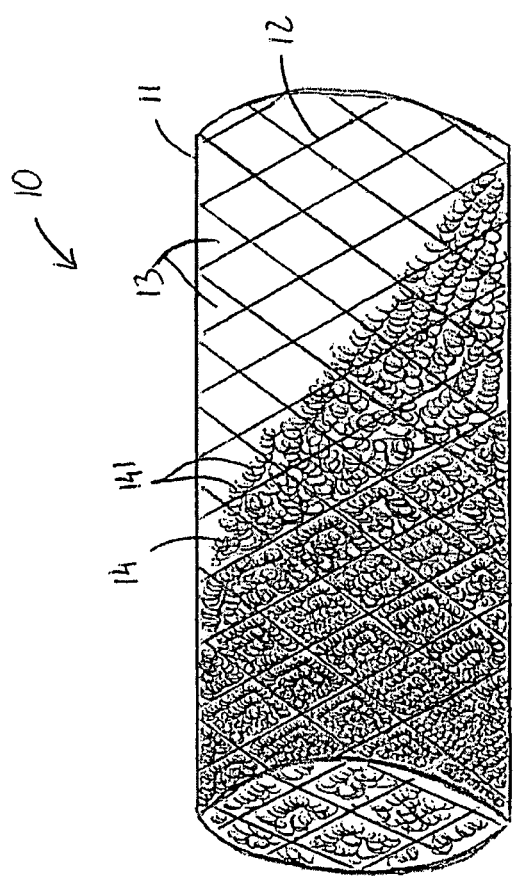
FIG. 1 illustrates a side view of an intravascular device in accordance with one embodiment of the present invention.

As illustrated in FIG. 1, there is shown in accordance with an embodiment of the present invention, an expandable intravascular device, such as a stent, for keeping open a lumen of a previously constricted intravascular site and for minimizing tissue debris from such a site from closing off the lumen. The device, in an embodiment, may also be used for local delivery of at least one pharmacotherapeutic agent to the intravascular site for the treatment or prevention of restenosis resulting from thrombus formation.

The intravascular device 10, as illustrated in FIG. 1, includes a substantially tubular body 11 for placement against a vessel wall and structural support thereof. The body 11, in an embodiment, may be defined by an expandable framework 12 having a plurality of openings 13. As the stent 10 is used to maintain an opening at a site which may have been previously constricted to provide a passage therethrough, the expandable framework 12 of stent 10 needs to be made from a biocompatible material that is sufficiently strong to maintain and support the opening. In one embodiment of the invention, a material from which the framework 12 may be made includes a metal, a metal alloy, plastic, or a combination thereof. By providing the stent 10 with, for instance, a metallic framework 12, the stent 10 may also be visualized, for example, by fluoroscopy during placement of the stent 10 within a vessel. Of course, the framework 12 may be made from other strong materials, for instance, polymeric materials that are well known in the art.

The stent 10 may also include a flexible netting system 14 extending across each of the openings 13 on framework 12. Since the stent 10 may be positioned at a previously constricted site, the presence of the netting system 14 on framework 12 can act to minimize the occurrence of tissue debris at such a site from being released into the lumen of the vessel and possibly closing off the lumen. In particular, the netting system 14 can act to retain tissue debris between it and the vessel wall. In one embodiment, as the flexible netting system 14 has elasticity, the netting system 14 may be allowed to radially extend through openings 13 and into the lumen of the vessel at from about 0.01 mm to about 0.5 mm. Although extending into the lumen, the netting system 14 may be designed so that such extension still permits about 75% to about 80% of the lumen to remain open for sufficient fluid flow through the vessel.

Still referring to FIG. 1, the netting system 14 may comprise a plurality of pores 141 to permit fluid communication between a vessel wall and fluid components within the vessel, such as blood. The pores 141, in an embodiment, may be displaced throughout the netting system 14 in similar or different patterns or shapes. For example, the netting system 14 may comprise a series of linked chains 22, as shown in FIG. 2A. In one embodiment, pores 141 may range from about 1/1000 to about 1/10 the size of an opening 13 in framework 12. Preferably, pores 141 may range from about 0.1 μm to about 100 μm. Regardless of the size, the pores 141 should act to permit fluid communication with the vessel wall while minimizing the occurrence of tissue debris from passing therethrough. In addition, is believed that the presence of pores 141 can provide proper tissue (e.g., endothelial cell) growth at, for example, a post-angioplasty stented site. Furthermore, the pores 141 may provide a space through which surrounding tissue may extend to secure the stent 10 in place.

The netting system 14 may also serve as a storage and direct transport vehicle for the local delivery of, for instance, thrombus-inhibiting pharmaceuticals To that end, the netting system 14 may be provided with a substantially uniform thickness and may be made from a biocompatible material, so as to minimize toxic reactions from surrounding tissues. The presence of the netting system 14 also provides additional surface area from which the pharmacotherapeutic agent can be eluted or delivered.

Examples of pharmacotherapeutic agents which may be incorporated within the netting system 14 include Rapamycin, a phospholipid exhibiting immunosuppressive properties. In addition, Heparin and glycosaminoglycans are anticoagulants which may be delivered locally after intravascular device implantation. These anticoagulants interact with growth factors and other glycoproteins, which may reduce neointimal proliferation.

Abciximab is a genetically engineered fragment of a chimeric human-murine mono-clonal antibody. It is a glycoprotein inhibitor and works by inhibiting the binding of fibrinogen and other substances to glycoprotein receptor (GBIIb/IIIa) on blood platelets integral to aggregation and clotting. Abciximab appears to be effective in preventing platelet aggregation when used with aspirin and heparin, and appears to be effective in preventing abrupt closure of arteries.

Antibiotics, likewise, can be used in the treatment of coronary artery disease. It is known that antibiotics are effective in controlling inflammation caused by a variety of infectious agents found in fatty plaques blocking the arteries. Azithromycin has been observed to provide modest antibiotic benefits for heart patients.

Other pharmacotherapeutic agents which can be incorporated into the netting system 14 includes radionuclides for use in the treatment of diseased tissues, and enzymes, which may be encapsulated within a carrier, for instance, a biodegradable sol-gel capsule dispersed within the netting system 14.

It should be appreciated that the concentration of pharmacotherapeutic agent or agents, as well as the rate of release can be adjusted according to the treatment for which the stent 10 is being used, so that the release rate of the agent or agents would be appropriate and sufficient for the treatment. For example, the netting system 14 may be coated with multiple layers, each having at least one pharmacotherapeutic agent dispersed therein.

Looking now at FIGS. 2A-B, the netting system 14 of the present invention may include a plurality of individual panels 21, each securely positioned within an opening 13 of framework 12. Each of the panels 21, in an embodiment, can include a structural design that provides it with sufficient strength to permit retention of tissue debris between the panel 21 and the vessel wall. In accordance with one embodiment, a structural design that can be implemented includes a series of extensible chained links 22 made from, for example, a metal, metal alloy, a polymer or a combination thereof. Such a design also permits each panel 21 to expand along with each opening 13 during expansion of the framework 12, as shown in FIG. 2B. Of course, other structural designs may be employed, so long as they permit each panel 21 to be sufficiently strong, expand accordingly, and retain tissue debris from falling into the lumen of the vessel.

Looking now at FIG. 3, there is illustrated a netting system 30 in accordance with another embodiment of the present invention. Netting system 30, as shown therein, may include a mesh 31, in a form of a sheet, for example, disposed on a substantially flexible matrix 32. By providing the netting system 30 with a flexible design, the netting system 30 may be placed circumferentially about the framework 12 of stent 10. Although flexible in design, it should be noted that the mesh 31 and matrix 32 structurally can provide the netting system 30 with sufficient strength to retain tissue debris between the netting system 30 and vessel wall 33. In addition, the utilization of the flexible matrix 32 can allow the mesh 31 thereon to expand along with the openings 13 during expansion of the framework 12. The netting system 30, in one embodiment, may be loosely positioned circumferentially about the framework 12. As such, the netting system 30 may be pulled onto framework 12 or pulled off framework 12 without damaging the netting system 30. It should be appreciated that although loosely positioned about the framework 12, subsequent to its expansion within a vessel, the netting system 30 may be pushed against the vessel wall 33 by the framework 12 to minimize movement of the netting system 30 thereat. Alternatively, the netting system 30 may be loosely secured to various sections of framework 12, for example, at multiple intersections 121 between filaments 122. Nevertheless, similar to the non-secured embodiment, the netting system 30 may be pushed against the vessel wall 33 by the framework 12 to remain secured thereat.

In accordance with another embodiment of the invention, the netting system 30 may be provided with enhanced rigidity to permit temporary support of the vessel wall until framework 12 can be expanded. With such a design, if necessary, the netting system 30 may be expanded at the site of interest initially independently of the framework 12. Thereafter, the framework 12, concentrically positioned within the netting system 30, may be expanded to provide the necessary support to the vessel wall. To provide the netting system 30 with a structural design sufficient to maintain the lumen of the vessel temporarily open, the flexible matrix 32 may be designed to include from about 50% to about 70% by volume of the filaments defining the framework 12. Of course, the amount of filaments making up the flexible matrix 32 can be less, so long as the matrix can temporarily keep the vessel wall from closing until the framework 12 can be expanded. In one embodiment, the strength and structural property of the netting system 30 can be calculated or adjusted by choice of materials, the amount (i.e., volume) of materials, or a combination thereof.

Figure 4:
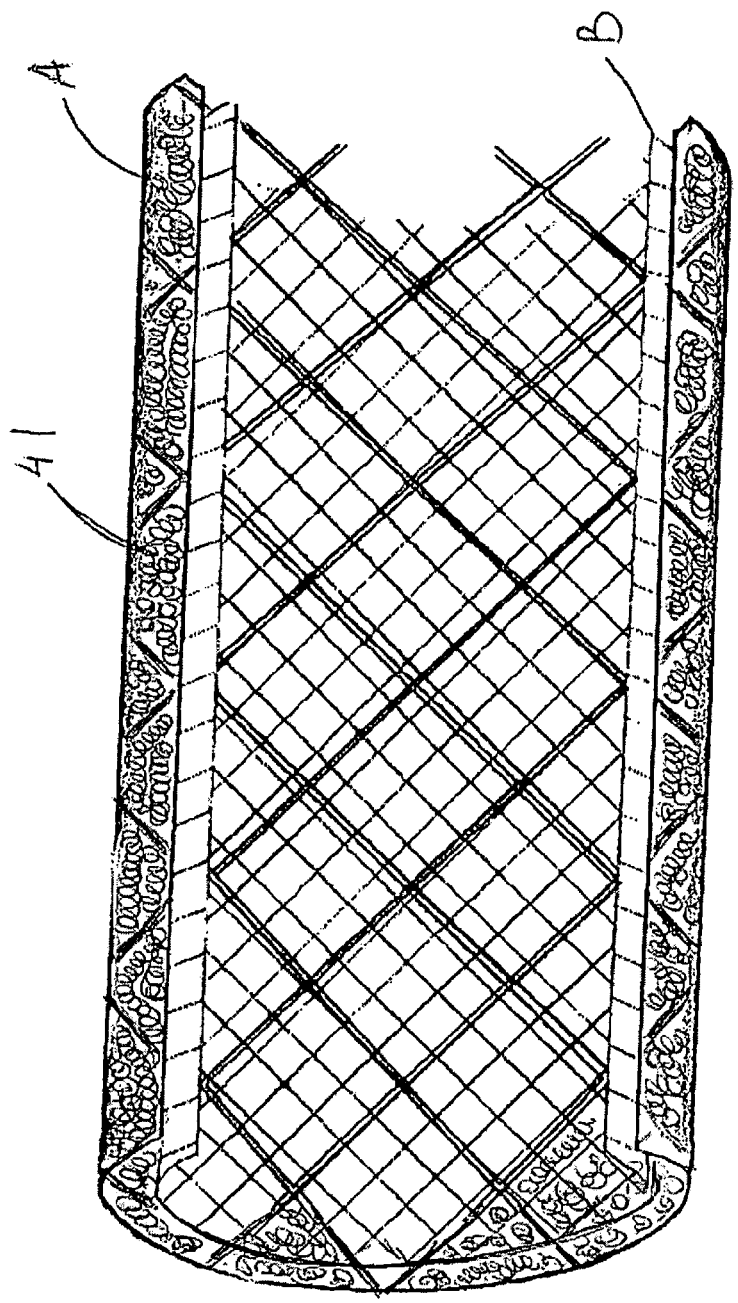
FIG. 4 illustrates a perspective view of an intravascular device having concentric frameworks in accordance with another embodiment of the present invention.

As an alternate embodiment, the netting system 30 may be a stent itself. In particular, looking now at FIG. 4, the netting system can be an outer stent A concentrically positioned about framework 12 (i.e., inner stent B). Although not illustrated as such, the two stents in this embodiment may be substantially similar to one another. The outer stent A or netting system 30, in one embodiment, may include individual panels 41, like the panels 21 shown in FIG. 2A, securely positioned within the openings of its framework. These panels 41, similar to panels 21, can act to retain tissue debris from falling into the lumen of the vessel, as well as to elute at least one of the pharmacotherapeutic agents noted above to a site of interest in order to minimize the occurrence of thrombus formation.

In use, intravascular device, such as stent 10 shown in FIG. 1, may be advanced along a lumen of a vessel to a site of interest, for example, a previously constricted site, an area where a cap may be thin, such as that associated with a vulnerable plaque, or a calcification site, such as that seen in carotid arteries. Thereafter, stent 10, and in particular, its framework 12, may be expanded at the site of interest to engage and support a wall of the vessel.

In the embodiment where the netting system is similar to flexible netting system 30, the framework 12 may be expanded at the site of interest, so that the netting system 30 may be expanded along therewith. Once the framework 12 is fully expanded, the netting system 30 may be secured between the framework 12 and the vessel wall.

In an alternate embodiment, where the netting system 30 may be sufficiently rigid, the netting system 30 may initially be expanded to engage the vessel wall to provide temporary support thereat. Subsequently, the framework 12, concentrically positioned within the expanded netting system 30, may be expanded to secure the netting system 30 between the vessel wall and the framework 12. A similar expansion protocol can be implemented in an embodiment where the netting system 30 may be a stent itself and a second stent exists concentrically therewithin.

Once the stent 10 has been expanded, the netting system may be permitted to facilitate the elution of at least one pharmacotherapeutic agent to the site of interest. In addition, the netting system may act to retain tissue debris between the netting system and a vessel wall.

Figure 5:
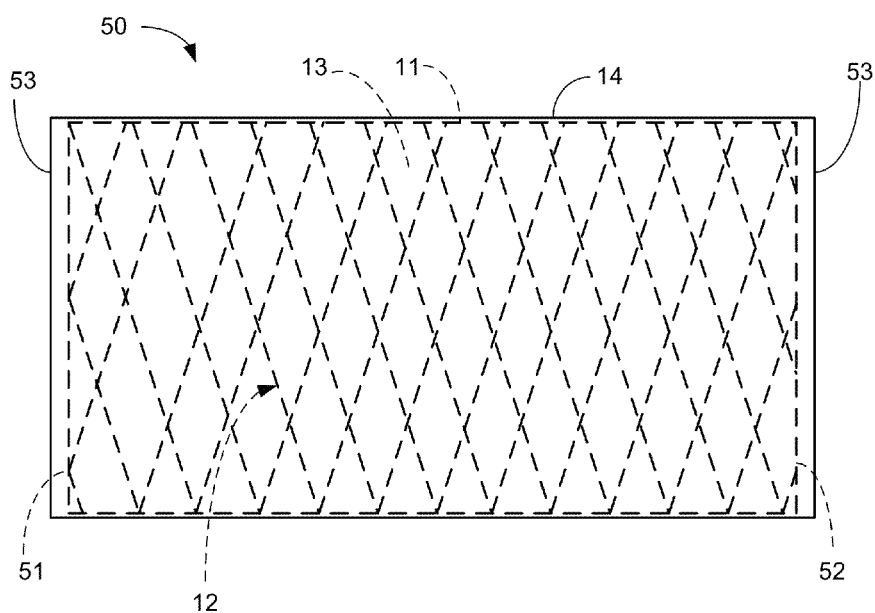
FIG. 5 illustrates an intravascular device having a netting system in accordance with an embodiment of the present invention.

In another embodiment illustrated in FIG. 5, the flexible netting system 14 and 30 described above, can be circumferentially disposed about the expandable tubular body 11, and can extend beyond a distal end 51 or a proximal end 52 of the tubular body 11. Alternatively, the netting system 14 can extend beyond both ends 51, 52 of the body 11. Generally, when a stent is deployed into a lumen and advanced through a vessel, there exists an inherent risk of abrasion or injury to the vessel wall. Typically, the abrasion can be caused by the edges of the rigid stent being pushed into the vessel wall during deployment. The extended portion 53 of the netting system 14 can mitigate this risk by serving as a cushion or barrier between the distal end 51 or proximal end 52 of the body 11 and the vessel wall. For example, if the device 10 is pushed into the vessel wall during deployment, the extended portion 53 of the flexible netting 14 contacts the vessel wall first, and can fold or collapse onto itself to serve as a cushion or barrier between the particular body end 51 or 52 of device 10 and the vessel wall. By mitigating the risk of abrasion and injury to the vessel wall, the extended portion 53 of the netting system 14 also can reduce the occurrence of thrombus formation, and tissue debris from closing the lumen of the vessel.

Oftentimes, after deployment and expansion of a stent, the vessel wall may develop an unsmooth landscape, such as bumps and protrusions, which in turn can cause the turbulent flow of blood in the vessel and injuries that can result in thrombus formation. The flexible netting system 14 with extended portions 53 can mitigate such damage to the vessel wall by serving as a porous barrier between the body 11 and the vessel wall. The netting system 14 with extended portions 53 can have a smooth surface, which can act to retain tissue debris between the netting system 14 and a vessel wall. This minimizes the protrusion of tissue into the lumen, and can therefore reduce turbulence of fluid flow within the lumen of the vessel.

Figure 6:
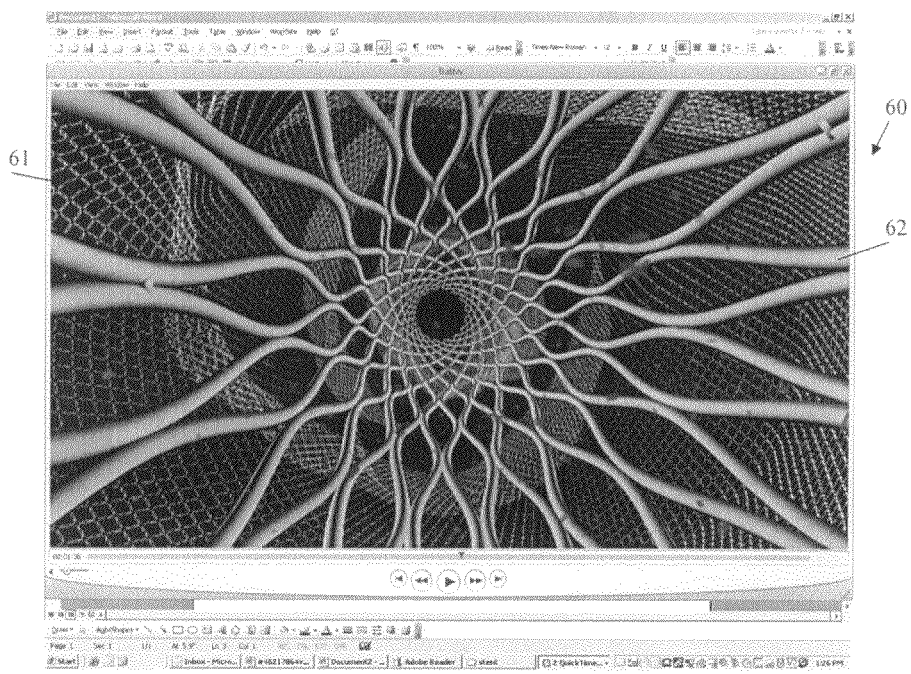
FIG. 6 illustrates an intravascular device configured as a double stent in accordance with an embodiment of the present invention.
Figure 7:
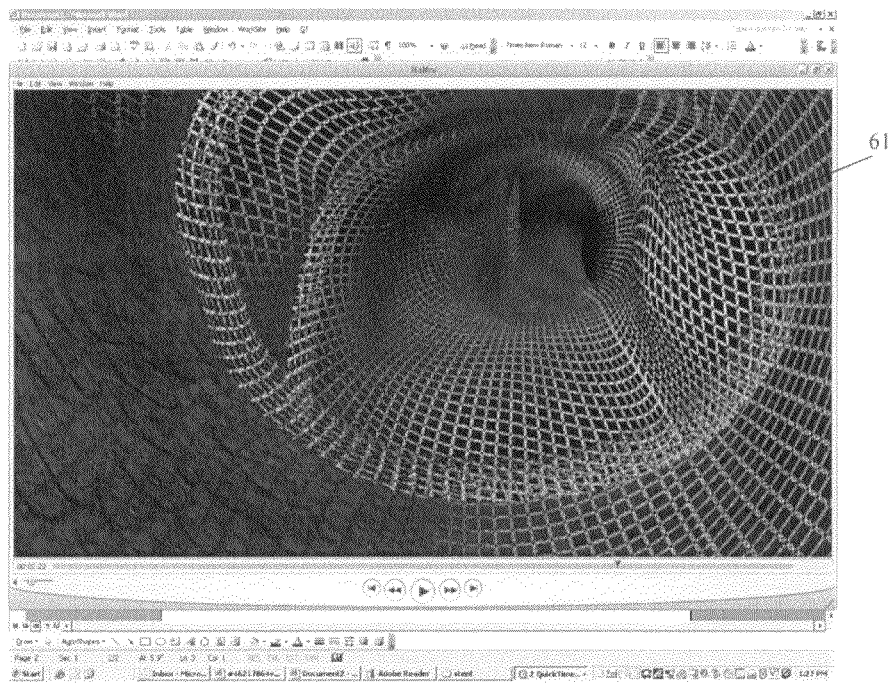
FIG. 7 illustrates an outer stent and netting system in accordance with an embodiment of the present invention.
Figure 8:
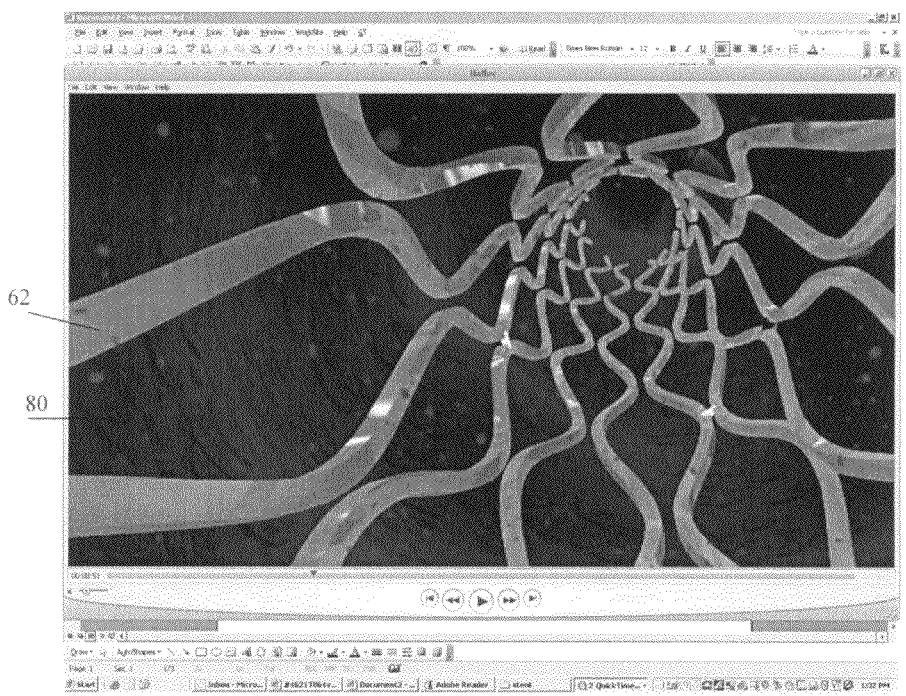
FIG. 8 illustrates an inner stent and expandable framework in accordance with an embodiment of the present invention.

In another embodiment illustrated in FIGS. 6 through 8, the present invention can be configured as a double stent 60, which can include an outer stent 61 having a smooth porous surface, and an inner stent 62 concentrically disposed within the outer stent 61. The outer stent 61 can have an inside diameter that can be substantially the same as the outside diameter of the inner stent 62. In an embodiment, the flexible netting system 14 or 30 can be the outer stent 61, and the expandable tubular body 11 can be the inner stent 62. The outer stent 61 can be circumferentially disposed about the inner stent 62 to minimize protrusion of tissue into the lumen, and to reduce turbulence of fluid flow within the lumen of the vessel. Similar to the flexible netting system 14, 30 discussed above, in an embodiment, the outer stent 61 can extend beyond the distal end 51, proximal end 52, or both ends of the inner stent 62. The extended portion 53 of the outer stent 61 can act as a barrier between the distal end 51 or proximal end 52 of the inner stent 62 and the vessel wall 80, to reduce risk of abrasion to the vessel wall 80 by the distal end 51 or proximal end 52 being pushed into the vessel wall 80 when the device 60 is advanced and expanded in the vessel.

In the figures, the outer stent 61 and flexible netting system 14, 30 are depicted as aggregations of interlaced rings or chain links. Those skilled in the art will appreciate that such a configuration is simply one embodiment presented for illustrative purposes only. Other structural configurations can be substituted for the interlaced rings, such as, interwoven mesh or intertwined threads and filaments. For example, the outer stent 61 and flexible netting system 14 can have a structural design that resembles that of the inner stent 62 or tubular body 11. Likewise, the inner stent 62 or tubular body 11 can have a structural design that resembles that of the outer stent 61 or flexible netting system 14.

The stent of the present invention may be used to support and maintain an opening within a variety of different vessels. For instance, the stent may be placed within a coronary artery or a carotid artery to facilitate fluid flow through such arteries. By facilitating fluid flow, a heart attack or a stroke may be avoided in patients who may have calcification or vulnerable plaques within their arteries as a result of aging, high blood pressure, diabetes or other similar physical conditions. The stent may also be used to constrict a passageway, for instance, the coronary sinus, among others. To constrict a passageway, the stent may be made so that it is substantially resistant to expansion, so as to permit the tubular framework to constrict the tubular framework around a passageway. The stent may also be used as a renal stent, gastrointestinal stent, radiation and chemotherapy stent. Further benefits of the present invention include reduced risk of trauma, smooth arterial walls, minimal debris formation, significantly reduced risk of thrombus formation, and reduced cost.

While the invention has been described in connection with the specific embodiments thereof, it will be understood that it is capable of further modification. For instance, the stent may be adapted for use with other intravascular devices for implantation within a patient's body. Furthermore, this application is intended to cover any variations, uses, or adaptations of the invention, including such departures from the present disclosure as come within known or customary practice in the art to which the invention pertains, and as fall within the scope of the appended claims.

What is claimed is:

1. An intravascular device for maintaining an open lumen within a vessel, the device comprising:
    an inner stent having an expandable substantially tubular body for placement against a vessel wall, the body having a longitudinally distal end and a longitudinally proximal end; and
    an outer stent having a smooth surface, the outer stent disposed circumferentially about the tubular body substantially co-extensively with the tubular body and configured to minimize protrusion of tissue into the lumen to reduce turbulence of fluid flow within the lumen of the vessel, the outer stent having an end that extends beyond at least one of the longitudinally distal end or the longitudinally proximal end, wherein the outer stent includes a plurality of pores therethroughout to permit communication between fluid flow within the vessel and the vessel wall.

2. A device as set forth in claim 1, wherein the outer stent has an inside diameter that is substantially the same as an outside diameter of the inner stent.

3. A device as set forth in claim 1, wherein the extended portion of the outer stent comprises a barrier between at least one of the longitudinally distal end or longitudinally proximal end of the body and the vessel wall, to reduce risk of abrasion to the vessel wall by the distal end or proximal end being pushed into the vessel wall when the device is advanced and expanded in the vessel.

4. A device as set forth in claim 1, wherein the outer stent is configured to fold or collapse onto itself about the longitudinally distal end or longitudinally proximal end of the body.

5. A device as set forth in claim 1 wherein the outer stent is configured to extend through openings of the tubular body from about 0.01 mm to about 0.5 mm.

6. A device as set forth in claim 1 wherein the outer stent is configured to permit at least about 75% to about 80% of a lumen of the tubular body to remain open in use.

7. An intravascular device for maintaining an open lumen within a vessel, the device comprising:
    an inner stent having an expandable substantially tubular body for placement against a vessel wall, the body having a longitudinally distal end and a longitudinally proximal end, the inner stent defining a plurality of openings through the inner stent disposed along a length of the inner stent; and
    an outer stent having a smooth surface, the outer stent disposed circumferentially about the tubular body and extending across each of the openings of the tubular body and configured to minimize protrusion of tissue into the lumen to reduce turbulence of fluid flow within the lumen of the vessel, the outer stent having an end that extends beyond at least one of the longitudinally distal end or the longitudinally proximal end, wherein the outer stent includes a plurality of pores therethroughout to permit communication between fluid flow within the vessel and the vessel wall.

8. A device as set forth in claim 7, wherein the outer stent has an inside diameter that is substantially the same as an outside diameter of the inner stent.

9. A device as set forth in claim 7, wherein the extended portion of the outer stent comprises a barrier between at least one of the longitudinally distal end or longitudinally proximal end of the body and the vessel wall, to reduce risk of abrasion to the vessel wall by the distal end or proximal end being pushed into the vessel wall when the device is advanced and expanded in the vessel.

10. A device as set forth in claim 7, wherein the outer stent is configured to fold or collapse onto itself about the longitudinally distal end or longitudinally proximal end of the body.

11. A device as set forth in claim 7 wherein the outer stent is configured to extend through openings of the tubular body from about 0.01 mm to about 0.5 mm.

12. A device as set forth in claim 7 wherein the outer stent is configured to permit at least about 75% to about 80% of a lumen of the tubular body to remain open in use.

* * * * *